US012806038B2

(12) United States Patent
Anderson et al.

(10) Patent No.: US 12,806,038 B2
(45) Date of Patent: Nov. 24, 2026

(54) ORTHOPAEDIC SURGICAL INSTRUMENT, SYSTEM, AND METHOD FOR INSTALLING A CEMENTED FEMORAL STEM COMPONENT IN A DIRECT ANTERIOR APPROACH HIP REPLACEMENT SURGICAL PROCEDURE

(71) Applicant: DePuy Ireland Unlimited Company, Ringaskiddy (IE)

(72) Inventors: James A. Anderson, York (GB); William P. Langenbach, Warsaw, IN (US); Soumyadeep Mukherjee, Leeds (GB); Amartya Sengupta, Leeds (GB)

(73) Assignee: DePuy Ireland Unlimited Company, Ringaskiddy (IE)

( * ) Notice: Subject to any disclaimer, the term of this patent is extended or adjusted under 35 U.S.C. 154(b) by 771 days.

(21) Appl. No.: 18/089,142

(22) Filed: Dec. 27, 2022

(65) Prior Publication Data

US 2024/0207067 A1 Jun. 27, 2024

(51) Int. Cl.
*A61F 2/46* (2006.01)
*A61B 17/88* (2006.01)

(52) U.S. Cl.
CPC ........ *A61F 2/4607* (2013.01); *A61B 17/8841* (2013.01); *A61F 2002/4622* (2013.01)

(58) Field of Classification Search
CPC ............................ A61F 2/4607; A61F 2/4612
See application file for complete search history.

(56) References Cited

U.S. PATENT DOCUMENTS

| | | | | |
|---|---|---|---|---|
| 4,293,962 | A | 10/1981 | Fuson | |
| 4,642,121 | A * | 2/1987 | Keller | A61F 2/4607 623/22.12 |
| 5,078,746 | A | 1/1992 | Garner | |
| 5,383,932 | A | 1/1995 | Wilson et al. | |
| 5,476,466 | A * | 12/1995 | Barrette | A61F 2/4607 606/86 R |
| 5,514,136 | A * | 5/1996 | Richelsoph | A61F 2/4607 606/86 R |
| 5,540,694 | A * | 7/1996 | DeCarlo, Jr. | A61B 17/175 606/80 |

(Continued)

FOREIGN PATENT DOCUMENTS

| | | | | |
|---|---|---|---|---|
| CN | 113558831 A * | 10/2021 | | A61F 2/4607 |
| DE | 4220970 A1 * | 7/1993 | | A61F 2/4607 |

(Continued)

OTHER PUBLICATIONS

C-STEM AMT Triple Tapered Stabilised Hip, Surgical Technique, 2020, 24 pages.

(Continued)

*Primary Examiner* — Alvin J Stewart
(74) *Attorney, Agent, or Firm* — Barnes & Thornburg LLP

(57) ABSTRACT

An orthopaedic surgical system for use in a direct anterior approach orthopaedic surgical hip replacement procedure on a patient's femur includes an insertion instrument having a depth stop with a rotatable guide arm to install a cemented femoral stem component at a desired depth. A method of installing a cemented femoral stem component during performance of a direct anterior approach orthopaedic surgical hip replacement procedure is also disclosed.

16 Claims, 9 Drawing Sheets

(56) References Cited

U.S. PATENT DOCUMENTS

| | | | | | |
|---|---|---|---|---|---|
| 5,743,910 | A * | 4/1998 | Bays | A61F 2/4607 606/99 |
| 5,792,143 | A * | 8/1998 | Samuelson | A61F 2/4607 606/102 |
| 5,951,606 | A * | 9/1999 | Burke | A61B 17/175 623/23.15 |
| 5,972,034 | A | 10/1999 | Hofmann et al. | |
| 5,989,259 | A * | 11/1999 | Penenberg | A61F 2/4657 606/102 |
| 6,110,179 | A * | 8/2000 | Flivik | A61B 17/8808 606/94 |
| 6,113,605 | A * | 9/2000 | Storer | A61F 2/4607 606/86 R |
| 6,165,177 | A * | 12/2000 | Wilson | A61F 2/4607 606/100 |
| 6,224,605 | B1 * | 5/2001 | Anderson | A61B 17/1659 606/85 |
| 6,330,845 | B1 * | 12/2001 | Meulink | A61B 17/8875 606/104 |
| 6,626,913 | B1 * | 9/2003 | Mckinnon | A61F 2/367 606/86 R |
| 7,601,155 | B2 * | 10/2009 | Petersen | A61B 17/175 606/85 |
| 7,854,737 | B2 * | 12/2010 | Daniels | A61F 2/4657 623/20.35 |
| 8,690,880 | B2 * | 4/2014 | Bastian | A61B 17/164 606/85 |
| 9,737,405 | B2 * | 8/2017 | Carr | A61F 2/30734 |
| 2002/0065518 | A1 | 5/2002 | Naybour et al. | |
| 2002/0156481 | A1 * | 10/2002 | Boyd | A61B 17/1757 606/90 |
| 2003/0220698 | A1 * | 11/2003 | Mears | B25B 7/02 623/22.4 |
| 2004/0267267 | A1 * | 12/2004 | Daniels | A61B 17/1617 623/22.42 |
| 2005/0033444 | A1 * | 2/2005 | Jones | A61F 2/4637 623/22.12 |
| 2005/0203539 | A1 * | 9/2005 | Grimm | A61F 2/4607 606/99 |
| 2007/0179630 | A1 * | 8/2007 | Benedict | A61B 17/8808 623/23.22 |
| 2007/0233134 | A1 * | 10/2007 | Bastian | A61F 2/4607 606/85 |
| 2008/0172061 | A1 * | 7/2008 | Ragbir | A61F 2/4603 606/208 |
| 2014/0094923 | A1 * | 4/2014 | Huff | A61F 2/367 623/20.35 |
| 2015/0057666 | A1 * | 2/2015 | Kelley | A61B 17/175 606/87 |
| 2016/0206445 | A1 * | 7/2016 | Gheevarughese | A61F 2/36 |
| 2022/0117756 | A1 * | 4/2022 | Blaser | A61F 2/4607 |
| 2023/0172622 | A1 * | 6/2023 | Wright | A61B 17/1604 606/84 |
| 2024/0180565 | A1 * | 6/2024 | Wright | A61B 17/162 |
| 2024/0293238 | A1 * | 9/2024 | Patnelli | A61F 2/3662 |
| 2024/0335293 | A1 * | 10/2024 | Saueressig | A61B 17/92 |
| 2024/0341978 | A1 * | 10/2024 | Wogoman | A61F 2/4609 |
| 2025/0025221 | A1 * | 1/2025 | Atkin | A61F 2/4603 |
| 2025/0325381 | A1 * | 10/2025 | Dun | A61F 2/4607 |

FOREIGN PATENT DOCUMENTS

| | | | | |
|---|---|---|---|---|
| EP | 0379785 | A1 | 8/1990 | |
| EP | 0626155 | A1 | 11/1994 | |
| EP | 1208821 | A2 | 5/2002 | |
| EP | 1459686 | A2 | 9/2004 | |
| EP | 1832248 | A2 * | 9/2007 | A61B 17/1659 |
| EP | 2786715 | A2 | 10/2014 | |
| JP | 3185273 | U * | 8/2013 | A61F 2/4607 |
| WO | 03065941 | A1 | 8/2003 | |
| WO | 2021130372 | A1 | 7/2021 | |

OTHER PUBLICATIONS

International Search Report and Written Opinion for International Application No. PCT/EP2023/087672, Mar. 27, 2024, 18 pages.

* cited by examiner

ORTHOPAEDIC SURGICAL INSTRUMENT, SYSTEM, AND METHOD FOR INSTALLING A CEMENTED FEMORAL STEM COMPONENT IN A DIRECT ANTERIOR APPROACH HIP REPLACEMENT SURGICAL PROCEDURE

TECHNICAL FIELD

The present disclosure relates generally to orthopaedic instruments, and particularly to orthopaedic instruments for use in a direct anterior approach hip replacement surgical procedure.

BACKGROUND

Joint arthroplasty is a well-known surgical procedure by which a diseased and/or damaged natural joint is replaced by a prosthetic joint. The prosthetic joint may include a prosthesis that is implanted into one or more of the patient's bones. Many hip prostheses include a femoral prosthesis that is implanted into a patient's femur. A femoral prosthesis typically includes an elongated stem component that is cemented in the medullary canal of the patient's femur and a spherically-shaped head component that bears against the patient's acetabulum or a prosthetic replacement acetabular cup.

Some hip replacement procedures are performed using a direct anterior approach. When using the direct anterior approach, the surgeon does not have line-of-sight access to the intramedullary canal of the patient's femur. This limited access and visibility makes it difficult for the surgeon to install certain components, such as cemented femoral stem components, using instruments designed for other approaches (e.g., a posterior approach).

SUMMARY

According to one aspect, an orthopaedic surgical instrument for implanting a cemented femoral stem component during a direct anterior approach orthopaedic hip replacement surgical procedure on a patient's femur includes a stem insertion instrument. The stem insertion instrument includes a handle positioned on a proximal end of the stem insertion instrument and an insertion prong positioned on a distal end of the stem insertion instrument. The insertion prong is sized and shaped to be received into an insertion aperture formed in a lateral shoulder of the femoral stem component. The insertion instrument also includes an elongated shaft extending distally away from the handle to the insertion prong and a depth stop rotatably secured to the elongated shaft. The depth stop includes a guide arm extending away from the elongated shaft.

In an embodiment, the depth stop includes a hub rotatably coupled to the elongated shaft and an extension arm extending distally away from the hub and transitioning to an elbow. In such an embodiment, the guide arm extends away from the elbow.

In an embodiment, the insertion prong extends in the superior/inferior direction, and the elongated shaft is angled in the medial direction relative to the insertion prong.

In another embodiment, a longitudinal axis of the insertion prong and a longitudinal axis of the elongated shaft define an offset angle, with such an offset angle being between 15-45 degrees.

In yet another embodiment, a longitudinal axis of the insertion prong and a longitudinal axis of the guide arm define a guide angle, with such a guide angle being between 40-45 degrees.

In an embodiment, the depth stop includes a second guide arm extending away from the elongated shaft from an opposite side of the elongated shaft as the other guide arm. In such an embodiment, the two guide arms may rotate relative to the elongated shaft independently of one another.

According to another aspect, an orthopaedic surgical system for use in a direct anterior approach orthopaedic hip replacement surgical procedure on a patient's femur includes a cemented femoral stem component and a stem insertion instrument. The cemented femoral stem component includes a proximal body that has a lateral shoulder. The lateral shoulder has an insertion aperture formed therein. The femoral stem component also include an elongated neck extending medially from the proximal body, and a tapered stem extending inferiorly away from proximal body. The stem insertion instrument includes a handle positioned on a proximal end of the stem insertion instrument, and an insertion prong positioned on a distal end of the stem insertion instrument. The insertion prong is sized and shaped to be received into the insertion aperture formed in the lateral shoulder of the femoral stem component. The insertion instrument also includes an elongated shaft extending distally away from the handle to the insertion prong, and a depth stop rotatably secured to the elongated shaft. The depth stop includes a guide arm extending away from the elongated shaft. When the insertion prong of the stem insertion instrument is positioned in the insertion aperture of the femoral stem component the depth stop is rotatable between a guide position in which the guide arm is positioned in contact with the femoral stem component, and an access position in which the guide arm is spaced apart from the femoral stem component.

In an embodiment, the guide arm is positioned in contact with an anterior side of the femoral stem component when the depth stop is positioned in its guide position.

In an embodiment, the guide arm is positioned in contact with an anterior side of the proximal body of the femoral stem component when the depth stop is positioned in its guide position.

In an embodiment, the depth stop includes a hub rotatably coupled to the elongated shaft and an extension arm extending distally away from the hub and transitioning to an elbow. In such an embodiment, the guide arm extends away from the elbow.

In an embodiment, the insertion prong extends in the superior/inferior direction, and the elongated shaft is angled in the medial direction relative to the insertion prong.

In another embodiment, a longitudinal axis of the insertion prong and a longitudinal axis of the elongated shaft define an offset angle, with such an offset angle being between 15-45 degrees.

In yet another embodiment, a longitudinal axis of the insertion prong and a longitudinal axis of the guide arm define an guide angle, with such a guide angle being between 40-45 degrees.

In an embodiment, the depth stop includes a second guide arm extending away from the elongated shaft from an opposite side of the elongated shaft as the other guide arm. In such an embodiment, when the insertion prong of the stem insertion instrument is positioned in the insertion aperture of the femoral stem component and the depth stop is positioned in its guide position, the first guide arm is positioned in contact with a first side of the femoral stem component and the second guide arm is positioned in contact with a second, opposite side of the femoral stem component. In a more specific example of such an embodiment, when the insertion prong of the stem insertion instrument is positioned in the insertion aperture of the femoral stem component and the depth stop is positioned in its guide position, the first guide arm is positioned in contact with an anterior side of the femoral stem component and the second guide arm is positioned in contact with a posterior side of the femoral stem component.

In an embodiment, the two guide arms may rotate relative to the elongated shaft independently of one another.

According to another aspect, a method of installing a cemented femoral stem component during performance of a direct anterior approach orthopaedic hip replacement surgical procedure on a patient's femur includes surgically-preparing a proximal end of the patient's femur so as to create a resected planar surface. An insertion prong of an insertion instrument is inserted into an insertion aperture formed in a lateral shoulder of the femoral stem component so as to secure the femoral stem component to the insertion instrument. A guide arm of the insertion instrument is rotated into contact with the secured femoral stem component. A distal end of the femoral stem component is then advanced through the surgically-prepared proximal end of the patient's femur and into an intramedullary canal of the patient's femur. The femoral stem component is then further advanced until the guide arm of the insertion instrument engages the resected planar surface of the surgically-prepared proximal end of the patient's femur.

In an embodiment, the guide arm of the insertion instrument is rotated into contact with an anterior surface of the secured femoral stem component.

In another embodiment, an anterior guide arm of the insertion instrument is rotated into contact with an anterior surface of the secured femoral stem component, and a posterior guide arm of the insertion instrument is rotated into contact with a posterior surface of the secured femoral stem component.

The guide arm may be rotated out of contact with the femoral stem component subsequent to engagement of the guide arm of the insertion instrument with the resected planar surface of the surgically-prepared proximal end of the patient's femur.

In an embodiment, the femoral stem component is unsecured from the insertion instrument subsequent to engagement of the guide arm of the insertion instrument with the resected planar surface of the surgically-prepared proximal end of the patient's femur, and thereafter the insertion prong of the insertion instrument is advanced proximally out of the intramedullary canal of the patient's femur.

BRIEF DESCRIPTION OF THE DRAWINGS

The detailed description particularly refers to the following figures, in which.

DETAILED DESCRIPTION OF THE DRAWINGS

Figure 1:
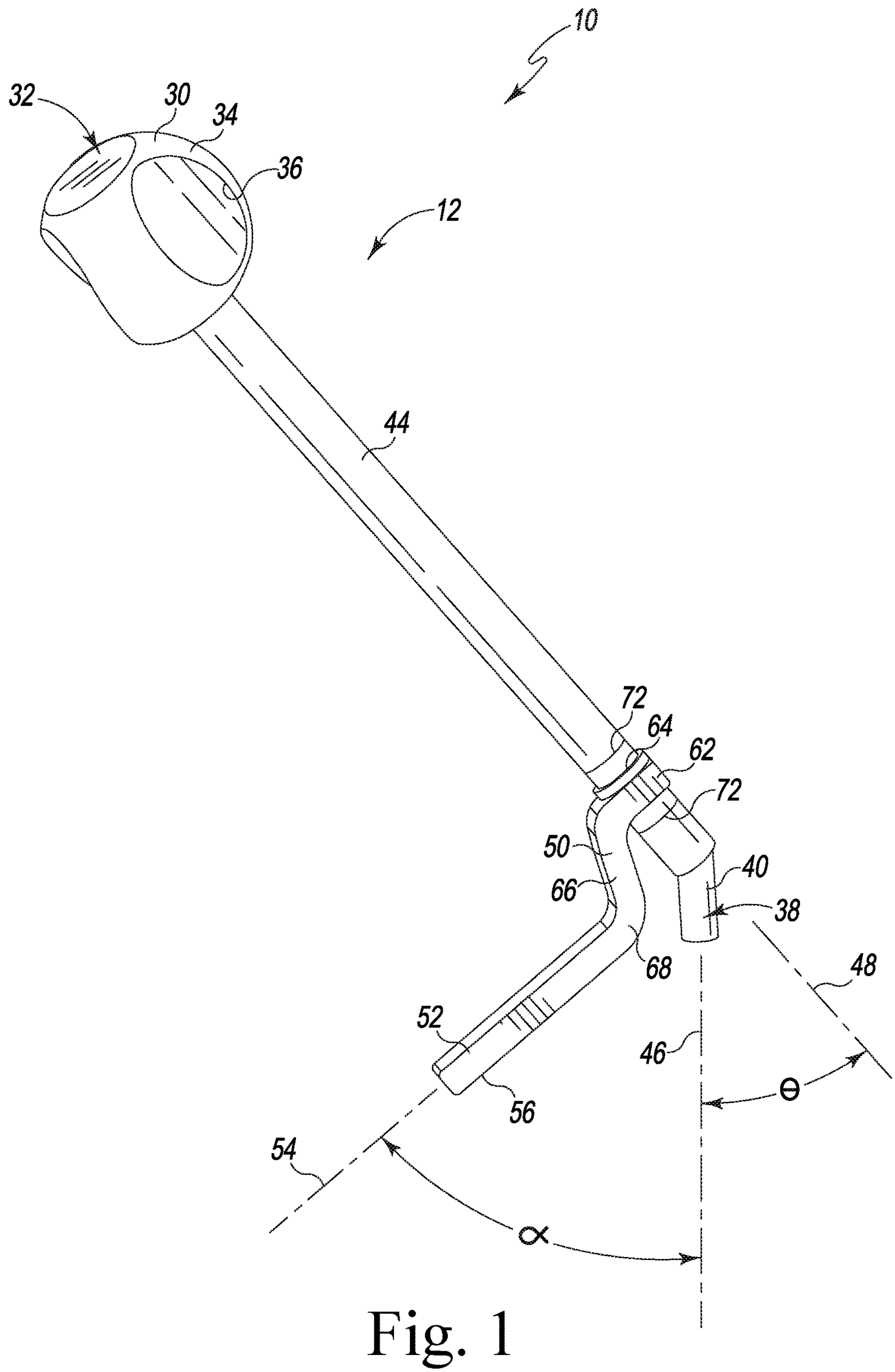
FIG. 1 is a perspective view of a stem insertion instrument of an orthopaedic surgical system for use in a direct anterior approach orthopaedic surgical hip replacement procedure on a patient's femur.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopedics. Use of such anatomical reference terms in the written description and claims is intended to be consistent with their well-understood meanings unless noted otherwise.

Figure 2:
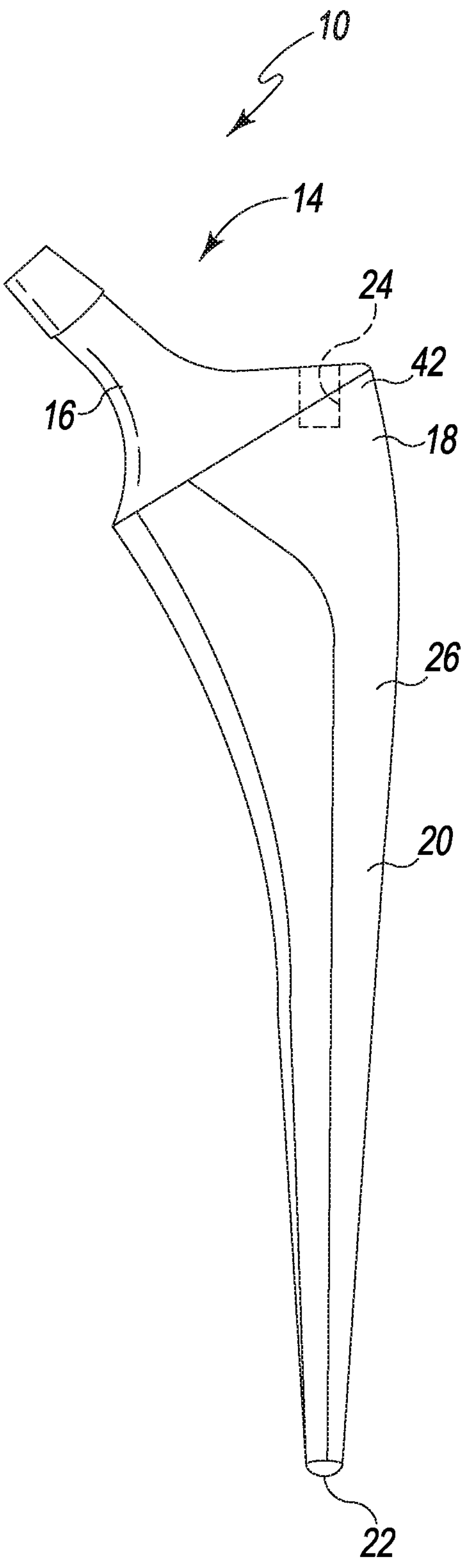
FIG. 2 is a side elevational view of a cemented femoral stem component.
Figure 3:
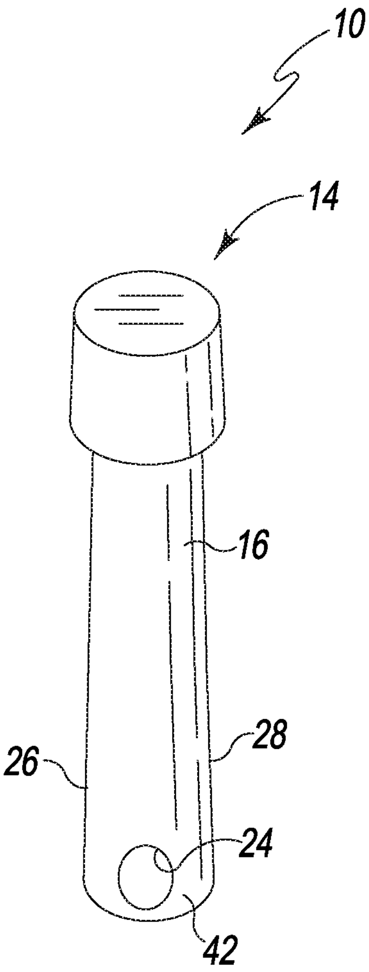
FIG. 3 is a top elevational view of the cemented femoral stem component of FIG. 2.

Referring to FIGS. 1-3, an orthopaedic surgical system 10 is illustratively embodied to include an insertion instrument 12 and a femoral stem component—specifically, a cemented femoral stem component 14. As will be discussed below in more detail, the insertion instrument 12 is used to install the femoral stem component 14 into an intramedullary canal of a patient's femur during a direct anterior approach hip replacement surgical procedure.

As shown in FIGS. 2 and 3, the femoral stem component 14 is configured to be implanted into the femur 106 of a patient during a hip replacement procedure. In particular, the femoral stem component 14 is implanted into a surgically-prepared (e.g., broached) intramedullary canal 104 of the patient's femur 106. A femoral head component (not shown) is secured to a trunnion formed in the end of the elongated neck 16 of the femoral stem component 14. When installed on the femoral stem component 14, the femoral head component is positioned to bear on either the patient's natural acetabulum or a prosthetic acetabular component which has been implanted into the patient's pelvis to replace his or her acetabulum. In such a manner, the femoral stem component 14 and the natural or artificial acetabulum collectively function as a system which replaces the natural joint of the patient's hip.

A proximal body 18 defines the midsection of the femoral stem component 14. As such, the elongated neck 16 extends superiorly and medially away from the proximal body 30, with the tapered trunnion being formed in the superior/medial end of the neck 16—i.e., opposite the end that mates with the proximal body 18. A tapered stem 20 extends inferiorly away from the opposite end of the proximal body 18. The tapered stem 20 has a rounded distal end 22 that defines the inferior-most surface of the femoral stem component 14. As can be seen in FIGS. 2 and 3, an insertion aperture 24 is formed in the proximal body's lateral shoulder 42. As will be discussed below in greater detail, the insertion aperture 24 frictionally receives an insertion prong of the insertion instrument 12 during installation of the femoral stem component 12.

In the illustrative embodiment described herein, the femoral stem component 14 is embodied as a cemented femoral stem—i.e., a stem that is installed with the use of bone cement. As such, the femoral stem component 14 is embodied as a monolithic metal structure. The femoral stem component 14 may be constructed with an implant-grade biocompatible metal, although other materials may also be used. Examples of such metals include cobalt, including cobalt alloys such as a cobalt chrome alloy, and stainless steel.

As can be seen in FIG. 1, the insertion instrument 12 has a handle 30 at its proximal end 32. In the illustrative embodiment of FIGS. 1-10 and 12, the handle 30 is embodied as a generally spherically-shaped knob 34 having a number of grip indentations 36 formed therein. The indentations 36 facilitate the surgeon's grip on the insertion instrument 12 by defining grip surfaces for the surgeon's individual fingers. It should be appreciated that the handle 30 may be embodied in numerous other configurations to fit the needs of a given design. For example, the handle 30 may be configured as a generally cylindrically-shaped grip or an elongated oval-shaped grip. The opposite distal end 38 of the insertion instrument 12 has an insertion prong 40. The insertion aperture 24 of the femoral stem component 14 is sized and shaped to frictionally receive the insertion prong 40 of the distal end 38 of the insertion instrument 12 to selectively secure the cemented femoral stem component 14 to the insertion instrument 12.

An elongated shaft 44 extends distally away from the center of the handle 30 towards the distal end 38 of the insertion instrument 12. The handle 30, the elongated shaft 44, and the insertion prong 40 may be integrally formed with one another, or may be provided as separate components welded or otherwise secured to one another.

Figure 5:
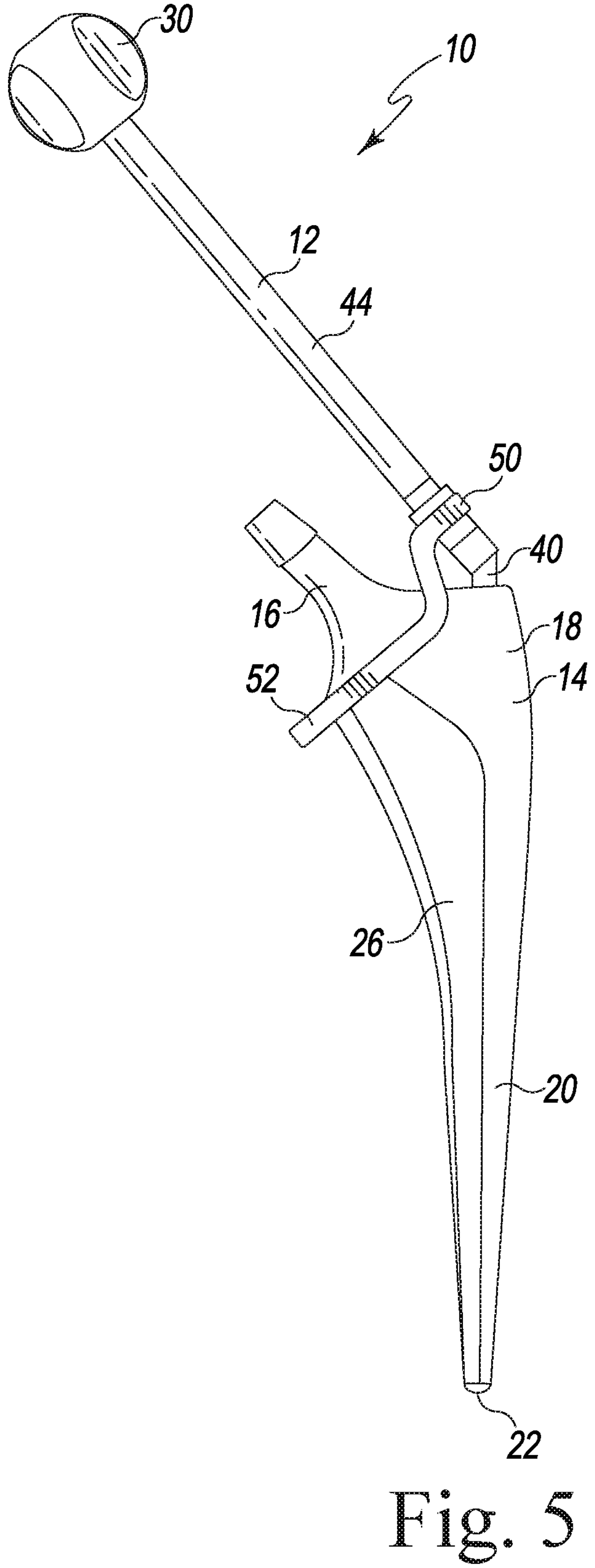
FIG. 5 is an anterior elevational view showing the stem insertion instrument of FIG. 1 secured to the femoral stem component of FIGS. 2 and 3.

To facilitate a direct anterior approach hip arthroplasty, the elongated shaft 44 is angled in the medial direction relative to the insertion prong 40. Specifically, as can be best seen in FIGS. 1 and 5, the insertion prong 40 extends in the superior/inferior direction. The elongated shaft 44 is angled in the medial direction relative to the insertion prong 40. In other words, as shown in FIG. 5, the elongated shaft 44 extends away from the proximal end of the insertion prong 40 in the medial direction. As will be discussed below, such an arrangement causes the insertion instrument 12 to extend medially when secured to the femoral stem component 14. As can be seen in FIG. 1, the longitudinal axis 46 of the insertion prong 40 and the longitudinal axis 48 of the elongated shaft 44 define an offset angle θ. In the illustrative embodiment described herein, the offset angle θ of the insertion instrument 12 is between 15-45 degrees. In a specific illustrative embodiment, the offset angle θ of the insertion instrument 12 is 30 degrees. Such medial offsetting of the insertion instrument 12 allows the insertion instrument 12 to facilitate the installation of the femoral stem component 14 "around the corner" of the proximal end 108 of a patient's femur 106 despite not having line-of-sight access to the intramedullary canal 104 during a direct anterior approach hip arthroplasty (see FIGS. 6-8).

As can be seen in FIG. 1, the insertion instrument 12 has a depth stop 50 rotatably secured to its elongated shaft 44 at a location between handle 30 and the insertion prong 40. As will be described in more detail below, the depth stop 50 engages a surgically-prepared resected planar surface 102 of the patient's femur 106 when the femoral stem component 14 has been advanced into the intramedullary canal 104 of the patient's femur 106 to a desired depth during installation thereof. The depth stop 50 includes a guide arm 52 extending away from the elongated shaft 44. As can be seen in FIGS. 1 and 5-7, the guide arm 52 has a longitudinal axis 54 that is parallel to the resection angle of the femoral stem component 14 and, as a result, is parallel to the surgically-prepared resected planar surface 102 of the patient's femur 106 onto which the femoral stem component 14 is to be implanted. In such a way, as can be seen in FIG. 7, the distal-most planar surface 56 of the guide arm 52 is arranged parallel to the surgically-prepared resected planar surface 102 of the patient's femur 106 when the femoral stem component 14 is installed into the patient's femur 106 thereby providing a blunt stop surface to engage the bone when the femoral stem component 14 has been installed to the desired depth. As can be seen in FIG. 1, the longitudinal axis 46 of the insertion prong 40 and the longitudinal axis 54 of the guide arm 52 define a guide angle α. In the illustrative embodiment described herein, the guide angle α is between 40-45 degrees. In a specific illustrative embodiment, the guide angle α is 45 degrees.

The depth stop 50 includes a hub 62. The hub 62 has a bore 64 extending therethrough. In such a way, the hub 62 is received onto the shaft 44 thereby rotatably coupling the guide arm 52 to the elongated shaft 44. An extension arm 66 extends outwardly and distally from the hub 62 and transitions to an elbow 68. The guide arm 52 extends away from the elbow 68. Thus, rotation of the hub 62 relative to the shaft 44 causes rotation of the guide arm 52. Such a feature allows the depth stop 50 to be used to control the depth at which the femoral stem component 14 is installed, yet have the ability to move the depth stop 50 out of the surgeon's line of sight if the surgeon needs to visualize into the prepared bone to, for example, assess the position of the femoral stem component 14 within a cement mantle introduced into the bone. Specifically, the depth stop 50 is rotatable between a guide position in which the guide arm 52 is positioned in contact with the anterior side 26 the femoral stem component 14 (see FIGS. 4-7) so as to function as a depth stop during installation of the femoral stem component 14, and an access position in which the guide arm 52 is spaced apart from the anterior side 26 of the femoral stem component 14 (see FIG. 8) so as to allow the surgeon to have visual and/or physical access to the patient's surgically-prepared femur 106.

As can be seen in FIG. 1, the elongated shaft 44 has a number of depth marks 72 formed thereon at a locations above the insertion prong 40. Each of the depth marks 72 corresponds to a desired depth in which the femoral stem component 14 may be advanced into the intramedullary canal 104 of the patient's femur 106 during installation thereof. The hub 62 of the depth stop 50 may be positioned on the elongated shaft 44 at the depth mark 72 corresponding to the desired implantation depth of the femoral stem component 14. The hub 62 may be configured as an open ring that allows the hub 62 to be snapped on and off the elongated shaft 44 at the desired depth mark 72. Alternatively, the depth marks 72 may be embodied as annular grooves formed in the outer surface of the elongated shaft 44. In such an embodiment, the hub 62 may be embodied with an annular ring formed in its bore that is selectively captured in the annular grooves formed in the shaft 44 to position the depth stop 50 at the desired depth mark 72.

In use, the orthopaedic surgical system 10 may be used by a surgeon to install the cemented femoral stem component 14 in the intramedullary canal 104 of a patient's femur 106 during a direct anterior approach hip replacement surgical procedure. Prior to installation of the femoral stem component 14, the surgeon performs a number of pre-operative and intra-operative surgical steps to prepare the patient's femur 106 to receive the femoral stem component 14. For example, the surgeon uses a bone saw to surgically resect the patient's natural femoral head and create a surgically-prepared proximal end 108 of the patient's femur 106 that includes, amongst other features, a resected planar surface 102. The surgeon also assembles and installs a number of trial components and trials the fit and function of the components to be installed before implanting the femoral stem component 14. Immediately prior to installation of the femoral stem component 14, the surgeon injects pressurized bone cement into the intramedullary canal 104 of the patient's femur 106. Once bone cement has been injected into the intramedullary canal 104 of the patient's femur 106, the surgeon installs the femoral stem component 14 before the bone cement sets (i.e., partially or completely hardens).

Figure 4:
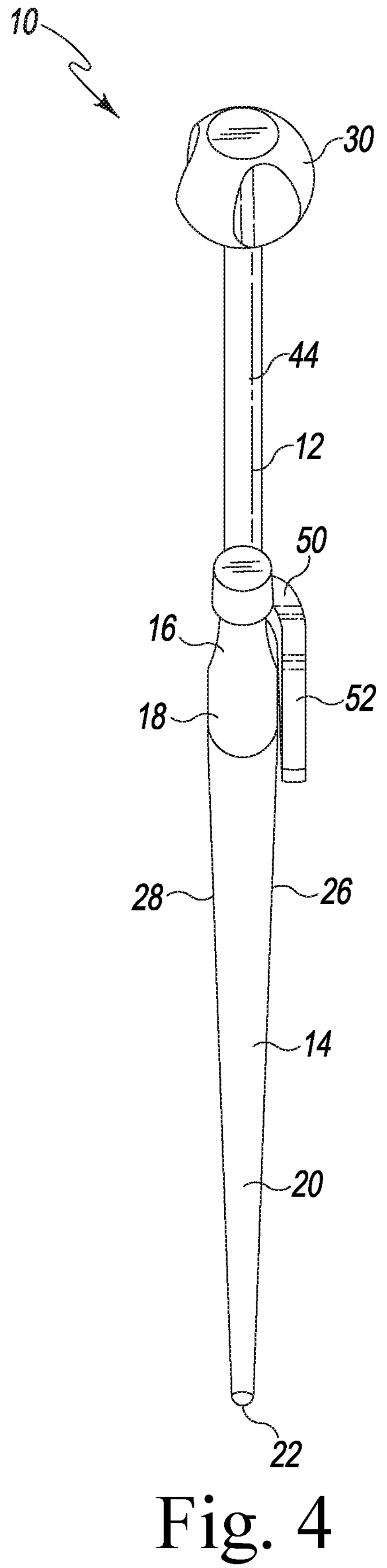
FIG. 4 is a medial elevational view showing the stem insertion instrument of FIG. 1 secured to the femoral stem component of FIGS. 2 and 3.

To do so, the surgeon first selects a femoral stem component 14 having the desired size from the various available sizes. The surgeon then installs the insertion instrument 12 to the selected femoral stem component 14. As such, the surgeon first positions the hub 62 of the instrument's depth stop at a location along the elongated shaft 44 at a depth mark 72 corresponding to the desired depth at which the femoral stem component 14 is to be implanted based on the surgeon's pre-operative and intra-operative analysis. Thereafter, the surgeon inserts the insertion prong 40 of the instrument 12 into the stem component's insertion aperture 24 (as shown in FIGS. 4 and 5). After doing so, the surgeon rotates the depth stop 50 of the insertion instrument 12 into its guide position in which the guide arm 52 is positioned in contact with the anterior side 26 the femoral stem component 14 (see FIGS. 4-7). In such a position, the guide arm 52 is arranged to function as a depth stop during installation of the femoral stem component 14.

Figure 6:
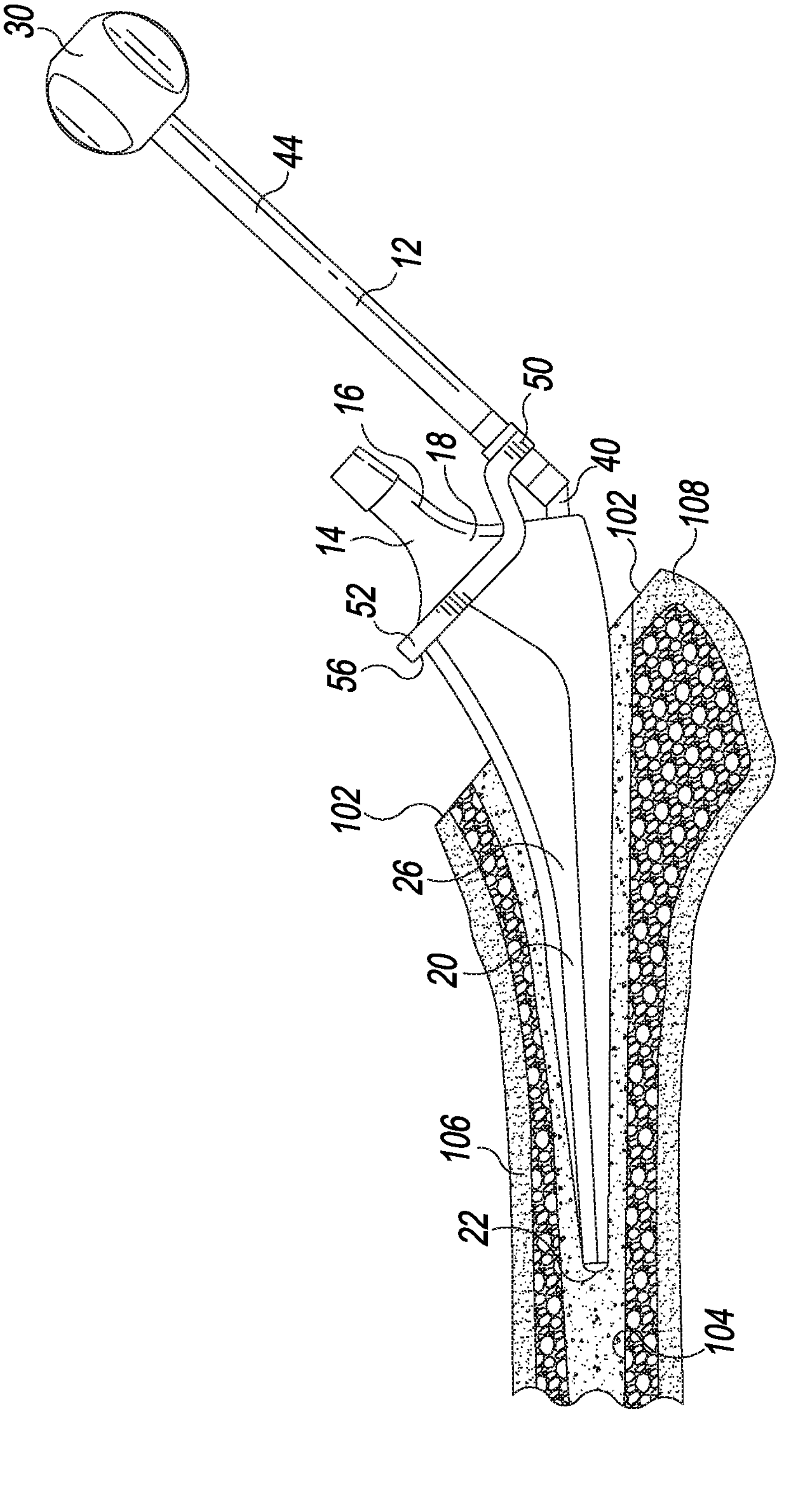
FIG. 6 is a cross-sectional view of a patient's femur during a direct anterior approach hip replacement surgical procedure, showing a surgeon introducing the femoral stem component of FIGS. 2 and 3 by use of the stem insertion instrument of FIG. 1.
Figure 7:
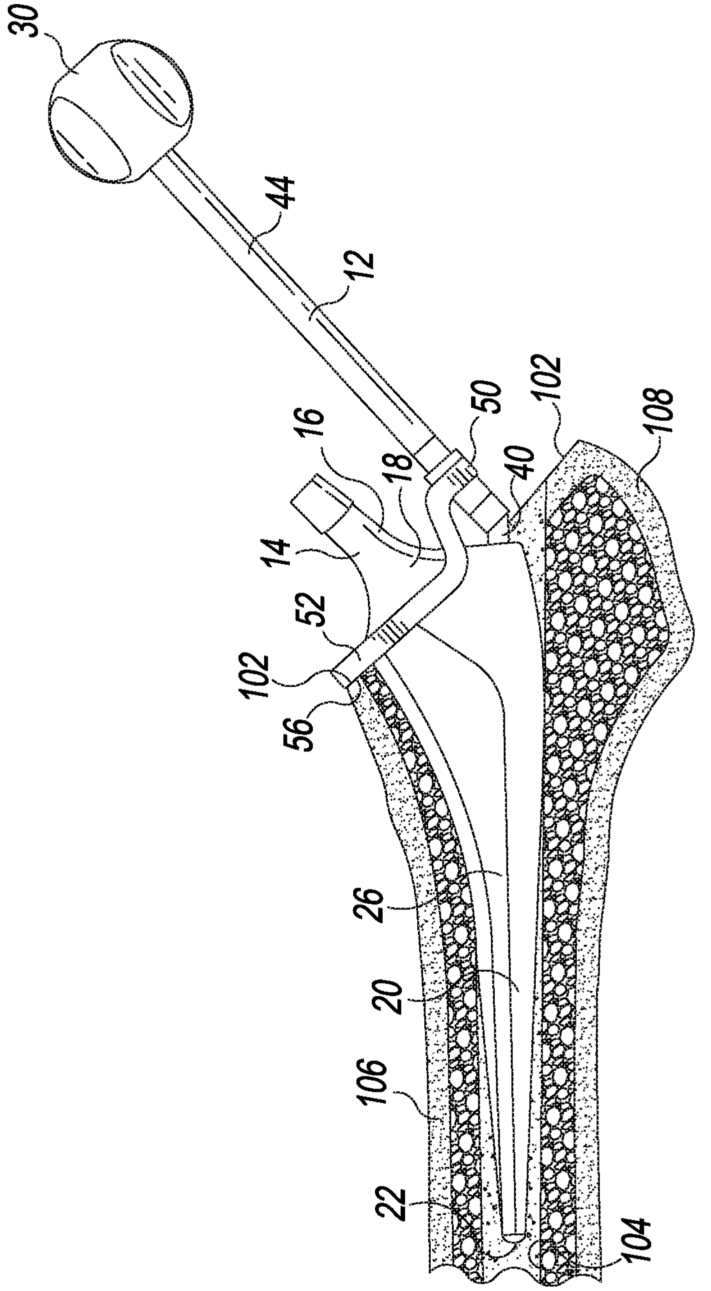
FIG. 7 is a view similar to FIG. 6, but showing the femoral stem component having reached a desired depth within the intramedullary canal of the patient's femur.
Figure 8:
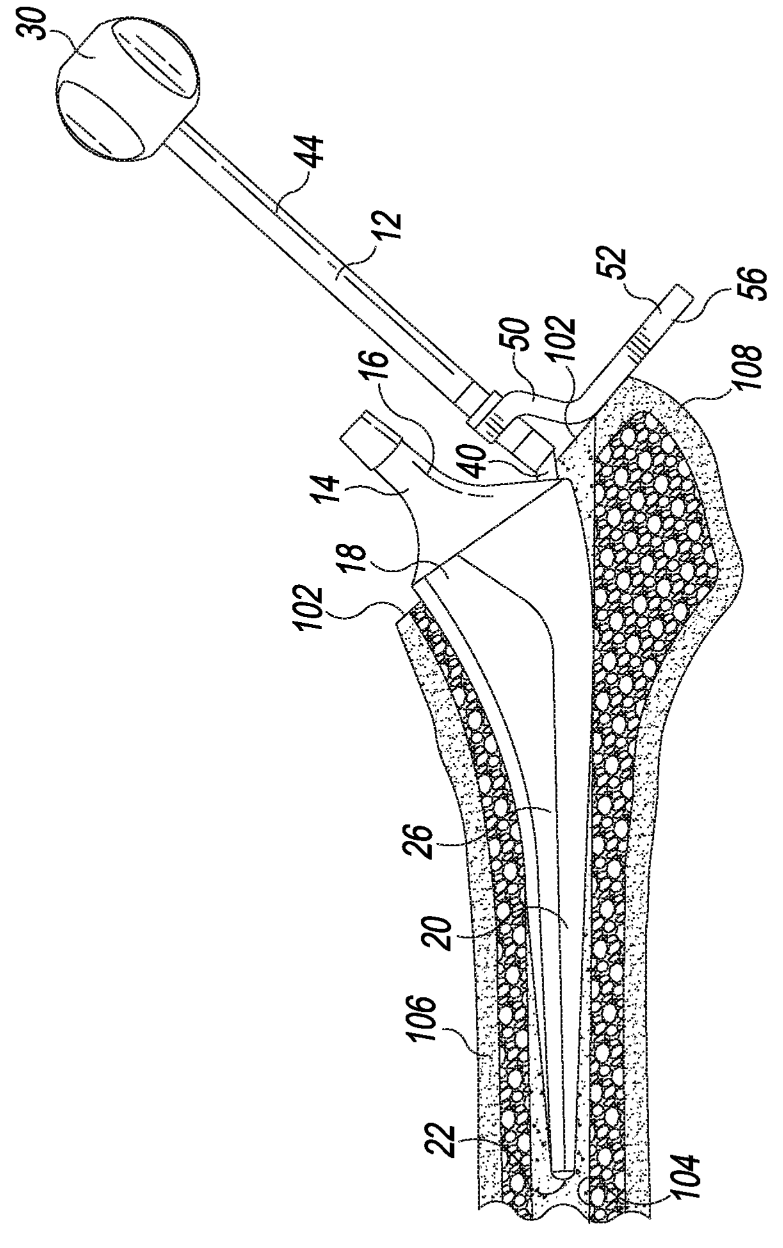
FIG. 8 is a view similar to FIG. 7, but showing the depth stop of the stem insertion instrument having been rotated to its access position.

Once the insertion instrument 12 is secured to the femoral stem component 14 with its depth stop 50 positioned in its guide position, as shown in FIG. 6, the surgeon advances the distal end 22 of the femoral stem component 14 through the surgically-prepared proximal end 108 of the patient's femur 106 and into the intramedullary canal 104. The surgeon grips the handle 30 and urges it distally toward the surgically-prepared proximal end 108 of the patient's femur 106. Doing so advances the femoral stem component 14 distally and thus further into the intramedullary canal 104 of the patient's femur 106. As shown in FIG. 6, during such advancement of the femoral stem component 14, the medial offset of the insertion instrument 12 (i.e., its elongated shaft 44 being angled medially when installed on the component 14) facilitates the surgeon's advancement of the femoral stem component 12 "around the corner" and into the proximal end 108 of the patient's femur 106 despite not having line-of-sight access to the intramedullary canal 104 during a direct anterior approach hip arthroplasty.

The surgeon continues to advance the handle 30 (and hence the femoral stem component 14) distally into the intramedullary canal 104 of the patient's femur 106 until the depth stop 50 engages bone. In particular, the surgeon continues to advance the femoral stem component 14 until the distal-most planar surface 56 of the guide arm 52 (see FIG. 7) engages the surgically-prepared resected planar surface 102 of the patient's femur 106 thus preventing further advancement of the insertion instrument 12 (and hence the femoral stem component 14). Engagement of the depth stop 50 with the surgically-prepared resected planar surface 102 of the patient's femur 106 provides an indication to the surgeon that the femoral stem component 14 has reached the desired depth.

Once the femoral stem component 14 has reached the desired depth, the surgeon then assesses if the femoral stem component 14 is properly positioned (e.g., centered) in the intramedullary canal 104. In order to do so, the surgeon may rotate the depth stop 50 to its access position in which the guide arm 52 is spaced apart from the anterior side 26 of the femoral stem component 14 (see FIG. 8) so as to allow the surgeon to have visual and/or physical access to the patient's surgically-prepared femur 106. The surgeon may do so by simply "flicking" the guide arm 52 out of the way with, for example, a cement curette or other instrument.

If the surgeon is satisfied with the fit of the femoral stem component 14 within the intramedullary canal 104, the surgeon pulls or otherwise urges the handle 30 in a direction away from the femoral stem component 14 while preventing movement of the femoral stem component 14 thereby releasing the instrument's insertion prong 40 from the stem component's insertion aperture 24. Once released in such a manner, the surgeon removes the insertion instrument 12 from the surgically-prepared proximal end 108 of the patient's femur. Thereafter, the surgeon performs the remaining steps in the surgical procedure.

Figure 9:
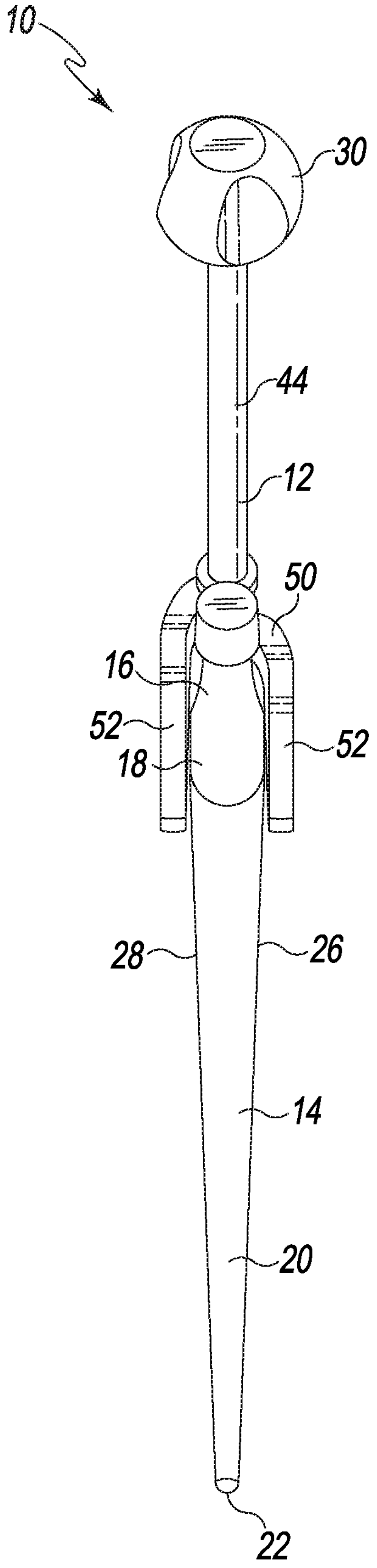
FIGS. 9 and 10 are similar to FIGS. 4 and 5, respectively, but showing the depth stop of the stem insertion instrument embodied with a second guide arm.
Figure 10:
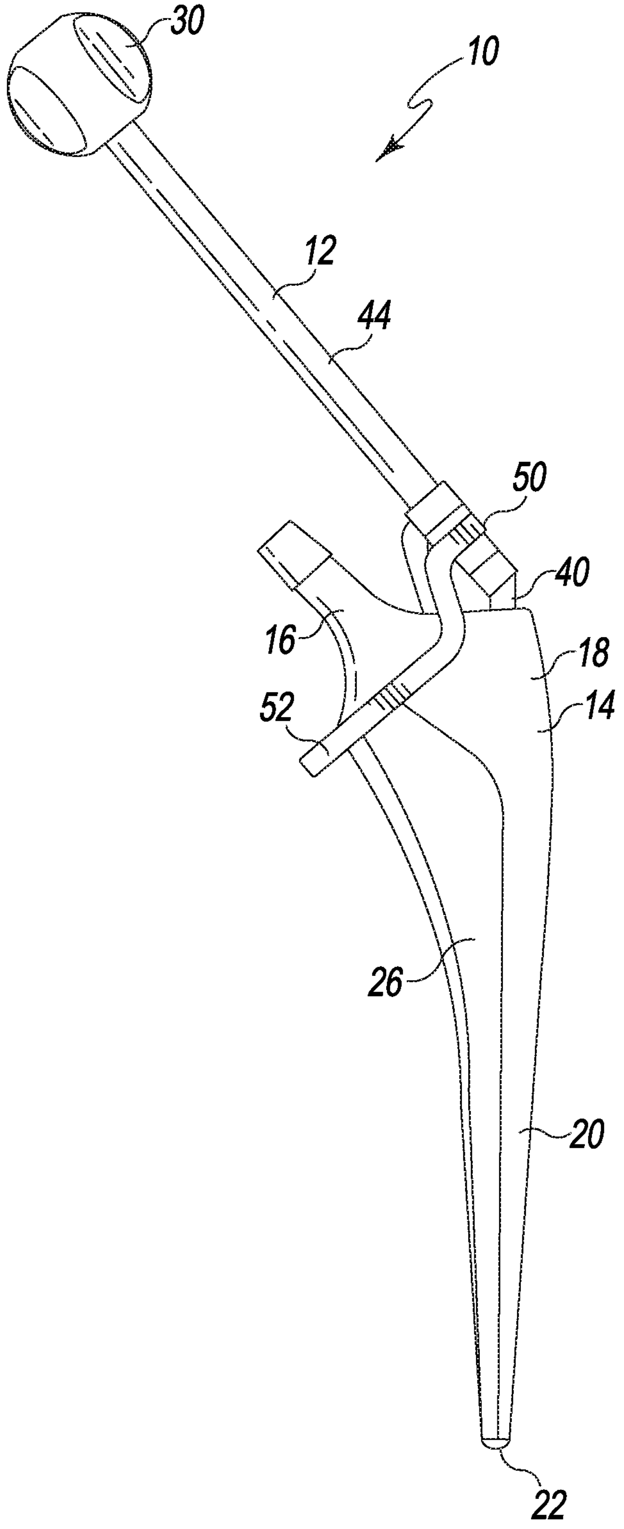

As shown in FIGS. 9 and 10, the depth stop 50 of the insertion instrument 10 may be embodied to provide depth guidance to both the anterior side 26 and the posterior side 28 of the femoral stem component 14. In particular, a second guide arm 52 (and associated hub 62 and extension arm 66) may be mounted on the opposite side of the elongated shaft 44. Like the anterior guide arm 52 of FIGS. 1-8, the posterior guide arm 52 extends away from the elongated shaft 44 and thus is generally arranged parallel to the anterior guide arm 52. The two guide arms 52 rotate relative to the elongated shaft 44 independently of one another and thus can be independently positioned by the surgeon in either the guide position or access position. When positioned in their respective guide positions, the anterior guide arm 52 contacts the proximal body 18 on the anterior side 26 of the stem component 14, whereas the posterior guide arm 52 contacts the opposite, posterior side 28 of the component's proximal body 18.

Figure 11:
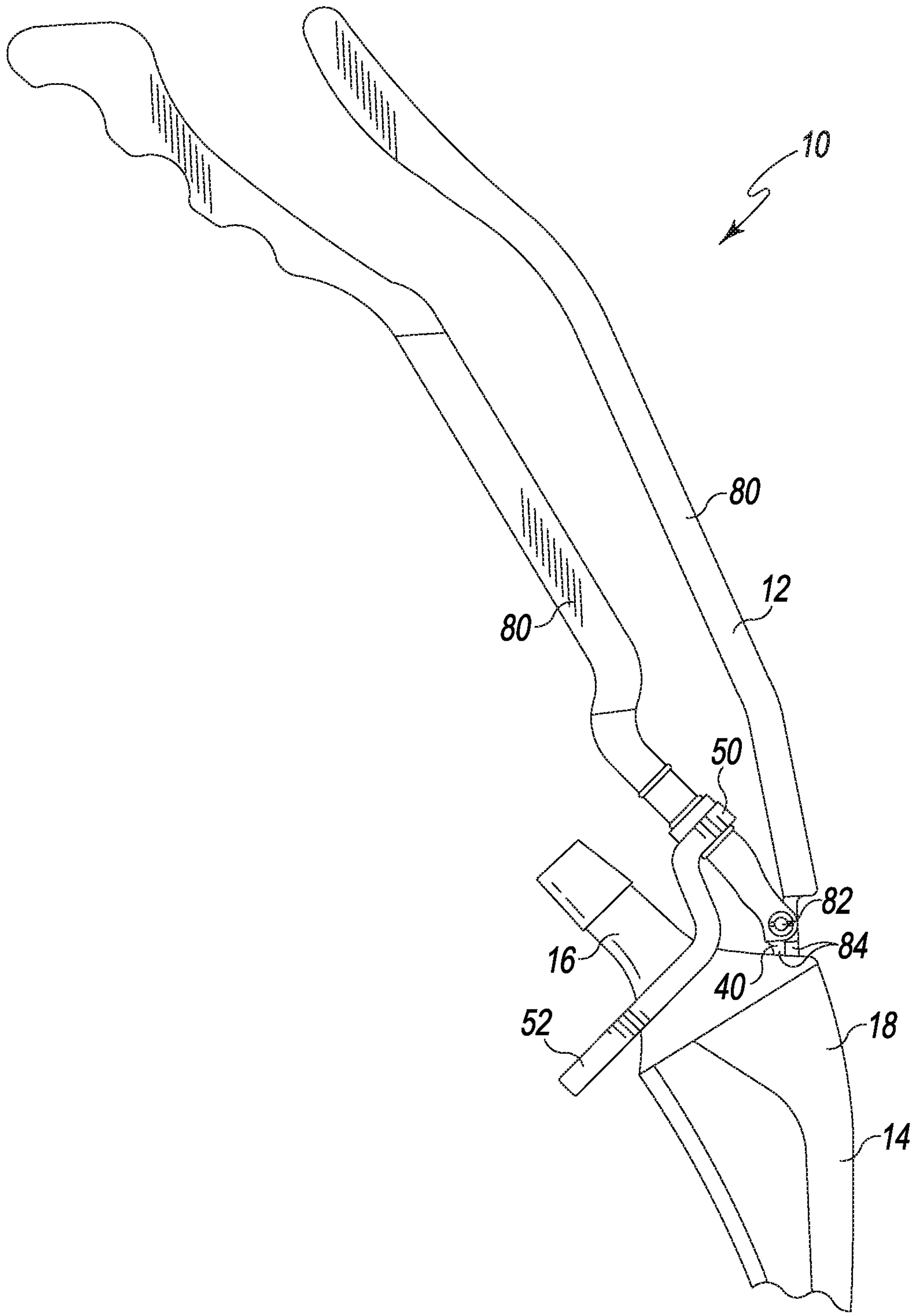
FIG. 11 is an elevation view of another embodiment of the stem insertion instrument.

As shown in FIG. 11, the insertion instrument 10 may be embodied to include a pair of handles 80 pivotally coupled to one another by a pivot joint 82. In such an embodiment, the insertion prong 40 is embodied as a pair of opposed jaws 84 that are moved away from one another when the handles 80 are squeezed by a user thereby providing enhanced mechanical retention of the femoral stem component 14 during installation thereof. It should be appreciated that although the embodiment of FIG. 11 is shown with a depth stop 50 that includes a single guide arm 52, the depth stop 50 may be embodied with dual guide arms similar to FIGS. 9 and 10.

Figure 12:
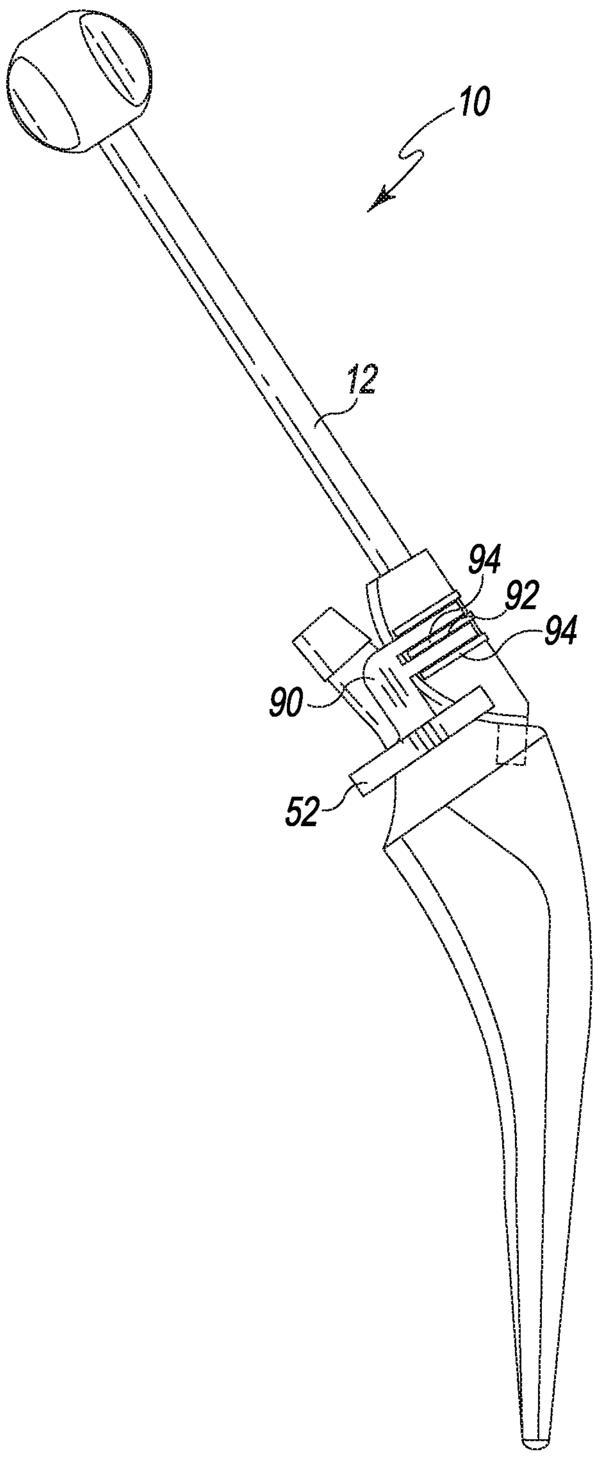
FIG. 12 is an elevation view of yet another embodiment of the stem insertion instrument.

As shown in FIG. 12, the insertion instrument 10 may be embodied to include a non-rotatable depth stop 50. In such an embodiment, the guide arm 52 is coupled to the distal end of the instrument by a bracket 90 that includes a slot 92 that slides on and off of a number of elongated rails 94 formed in the distal end of the instrument 10. As can be seen in FIG. 12, multiple rails 94 are used to provide for selecting varying implant depths similar to the depth marks 72 of the instrument of FIGS. 1-8. It should be appreciated that although the embodiment of FIG. 12 is shown with a depth stop 50 that includes a single guide arm 52, the depth stop 50 may be embodied with dual guide arms similar to FIGS. 9 and 10.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument for implanting a cemented femoral stem component during a direct anterior approach orthopaedic hip replacement surgical procedure on a patient's femur, comprising:

a stem insertion instrument comprising:

a handle positioned on a proximal end of the stem insertion instrument, an insertion prong positioned on a distal end of the stem insertion instrument, the insertion prong being sized and shaped to be received into an insertion aperture formed in a lateral shoulder of the femoral stem component, an elongated shaft extending distally away from the handle to the insertion prong along a longitudinal axis, and a depth stop rotatably secured to the elongated shaft to rotate about the longitudinal axis of the elongated shaft, the depth stop comprising a guide arm extending away from the elongated shaft, wherein a longitudinal axis of the insertion prong and a longitudinal axis of the guide arm define a guide angle, and the guide angle is between 40-45 degrees.

2. The orthopaedic surgical instrument of claim 1, wherein:

the depth stop further comprises: (i) a hub rotatably coupled to the elongated shaft, and (ii) an extension arm extending distally away from the hub and transitioning to an elbow, and the guide arm extends away from the elbow.

3. The orthopaedic surgical instrument of claim 1, wherein:

the insertion prong extends in the superior/inferior direction, and the elongated shaft is angled in the medial direction relative to the insertion prong.

4. The orthopaedic surgical instrument of claim 1, wherein:

the longitudinal axis of the insertion prong and the longitudinal axis of the elongated shaft define an offset angle, and the offset angle is between 15-45 degrees.

5. The orthopaedic surgical instrument of claim 1, wherein:

the guide arm comprises a first guide arm, the depth stop further comprises a second guide arm extending away from the elongated shaft from an opposite side of the elongated shaft as the first guide arm, and the first guide arm and the second guide arm rotate relative to the elongated shaft independently of one another.

6. The orthopaedic surgical instrument of claim 5, wherein the depth stop moves between a first position in which the first and second guide arms extend medially from the elongated shaft and a second position in which the first and second guide arms are rotated so as to extend laterally from the elongated shaft.

7. The orthopaedic surgical instrument of claim 1, wherein the depth stop is rotatably secured directly to the elongated shaft.

8. The orthopaedic surgical instrument of claim 1, wherein:

the depth stop further comprises: (i) a hub rotatably coupled to the elongated shaft and having a bore extending therethrough that receives the elongated shaft therein, and (ii) an extension arm extending distally away from the hub and transitioning to an elbow, and the first guide arm extends away from the elbow.

9. An orthopaedic surgical system for use in a direct anterior approach orthopaedic hip replacement surgical procedure on a patient's femur, comprising:

a cemented femoral stem component comprising (i) a proximal body that includes a lateral shoulder, the lateral shoulder having an insertion aperture formed therein, (ii) an elongated neck extending medially from the proximal body, and (iii) a tapered stem extending inferiorly away from proximal body, and a stem insertion instrument comprising (i) a handle positioned on a proximal end of the stem insertion instrument, (ii) an insertion prong positioned on a distal end of the stem insertion instrument, the insertion prong being sized and shaped to be received into the insertion aperture formed in the lateral shoulder of the femoral stem component, (iii) an elongated shaft extending distally away from the handle to the insertion prong, and (iv) a depth stop rotatably secured to the elongated shaft, the depth stop comprising a first guide arm extending away from the elongated shaft and a second guide arm extending away from the elongated shaft from an opposite side of the elongated shaft as the first guide arm, the first guide arm and the second guide arm rotate relative to the elongated shaft independently of one another, wherein when the insertion prong of the stem insertion instrument is positioned in the insertion aperture of the femoral stem component the depth stop is rotatable between (a) a guide position in which the first guide arm is positioned in contact with a first side of the femoral stem component and the second guide arm is positioned in contact with a second, opposite side of the femoral stem component, and (b) an access position in which the first and second guide arms are spaced apart from the femoral stem component.

10. The orthopaedic surgical system of claim 9, wherein the first guide arm is positioned in contact with an anterior side of the femoral stem component when the depth stop is positioned in its guide position.

11. The orthopaedic surgical system of claim 9, wherein the first guide arm is positioned in contact with an anterior side of the proximal body of the femoral stem component when the depth stop is positioned in its guide position.

12. The orthopaedic surgical system of claim 9, wherein:

the depth stop further comprises: (i) a hub rotatably coupled to the elongated shaft, and (ii) an extension arm extending distally away from the hub and transitioning to an elbow, and the first guide arm extends away from the elbow.

13. The orthopaedic surgical system of claim 9, wherein:

the insertion prong extends in the superior/inferior direction, and the elongated shaft is angled in the medial direction relative to the insertion prong.

14. The orthopaedic surgical system of claim 9, wherein:

a longitudinal axis of the insertion prong and a longitudinal axis of the elongated shaft define an offset angle, and the offset angle is between 15-45 degrees.

15. The orthopaedic surgical system of claim 9, wherein:

a longitudinal axis of the insertion prong and a longitudinal axis of the first guide arm define a guide angle, and the guide angle is between 40-45 degrees.

16. The orthopaedic surgical system of claim 9, wherein:

the first side of the femoral stem component is an anterior side of the femoral stem component and the second, opposite side of the femoral stem component is a posterior side of the femoral stem component.

* * * * *